US008691067B2

(12) United States Patent
Harrer et al.

(10) Patent No.: US 8,691,067 B2
(45) Date of Patent: *Apr. 8, 2014

(54) CHARGED ENTITIES AS LOCOMOTIVE TO CONTROL MOTION OF POLYMERS THROUGH A NANOCHANNEL

(75) Inventors: Stefan Harrer, New York, NY (US); Binquan Luan, Ossining, NY (US); Glenn J. Martyna, Croton on Hudson, NY (US); Hongbo Peng, Chappaque, NY (US); Stanislav Polonsky, Putnam Valley, NY (US); Stephen M. Rossnagel, Pleasantville, NY (US); Ajay k. Royyuru, Congers, NY (US); Gustavo A. Stolovitzky, Riverdale, NY (US); George F. Walker, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 152 days.

This patent is subject to a terminal disclaimer.

(21) Appl. No.: 13/234,276

(22) Filed: Sep. 16, 2011

(65) Prior Publication Data

US 2013/0068617 A1 Mar. 21, 2013

(51) Int. Cl.
*G01N 27/26* (2006.01)
(52) U.S. Cl.
USPC ......................................................... 204/451
(58) Field of Classification Search
USPC .................. 204/450, 451, 600, 403.01; 435/6
See application file for complete search history.

(56) References Cited

U.S. PATENT DOCUMENTS

| 5,607,691 A | 3/1997 | Hale et al. |
|---|---|---|
| 5,938,904 A | 8/1999 | Bader et al. |
| 6,352,838 B1 | 3/2002 | Krulevitch et al. |
| 6,537,433 B1 | 3/2003 | Bryning et al. |
| 2005/0218464 A1 | 10/2005 | Holm-Kennedy |
| 2006/0054503 A1* | 3/2006 | Pamula et al. ................ 204/450 |
| 2007/0190542 A1 | 8/2007 | Ling et al. |
| 2008/0053205 A1* | 3/2008 | Pollack et al. ............... 73/61.71 |

(Continued)

FOREIGN PATENT DOCUMENTS

| CN | 1667401 A | 9/2005 |
|---|---|---|
| CN | 102037351 A | 4/2011 |

OTHER PUBLICATIONS

Harrer, et al., pending U.S. Appl. No. 12/820,516 entitled "Nano-Fluidic Field Effective Device to Control DNA Transport Through the Same," field with the U.S. Patent and Trademark Office on Jun. 22, 2010.

(Continued)

*Primary Examiner* — J. Christopher Ball
(74) *Attorney, Agent, or Firm* — Cantor Colburn LLP; Vazken Alexanian

(57) ABSTRACT

A technique for controlling the motion of one or more charged entities linked to a polymer through a nanochannel is provided. A first reservoir and a second reservoir are connected by the nanochannel. An array of electrodes is positioned along the nanochannel, where fluid fills the first reservoir, the second reservoir, and the nanochannel. A first electrode is in the first reservoir and a second electrode is in the second reservoir. The first and second electrodes are configured to direct the one or more charged entities linked to the polymer into the nanochannel. An array of electrodes is configured to trap the one or more charged entities in the nanochannel responsive to being controlled for trapping. The array of electrodes is configured to move the one or more charged entities along the nanochannel responsive to being controlled for moving.

15 Claims, 7 Drawing Sheets

(56) References Cited

U.S. PATENT DOCUMENTS

| | | | |
|---|---|---|---|
| 2008/0187915 A1* | 8/2008 | Polonsky et al. | 435/6 |
| 2008/0230386 A1* | 9/2008 | Srinivasan et al. | 204/450 |
| 2009/0038939 A1 | 2/2009 | Popovich et al. | |
| 2010/0243449 A1* | 9/2010 | Oliver | 204/450 |
| 2011/0053794 A1 | 3/2011 | Zhang | |
| 2013/0068618 A1* | 3/2013 | Harrer et al. | 204/451 |
| 2013/0068622 A1 | 3/2013 | Schertzer et al. | |

OTHER PUBLICATIONS

Heller, et al., "Use of Electric Field Array Devices for Assisted Assembly of DNA Nanocomponents and Other Nanofabrication Applications", in "BioMEMS and Biomedical Nanotechnology", 2007, Springer US, pp. 137-159.

Kasianowicz, et al., "Characterization of Individual Polynucleotide Molecules Using a Membrane Channel", Proc. Natl. Acad. Sci. USA, vol. 93, 1996, pp. 13770-13773.

Polonsky, et al., "Nanopore in Metal-Dielectric Sandwich for DNA Position Control", Appl. Phys. Lett., vol. 91, 2007; pp. 153103-1-153103-3.

International Search Report and Written Opinon; International Application No. PCT/CN2012/078585; International Filing Date: Jul. 13, 2012; Earliest Priortiy Date: Sep. 16, 2011; 10 pages.

\* cited by examiner

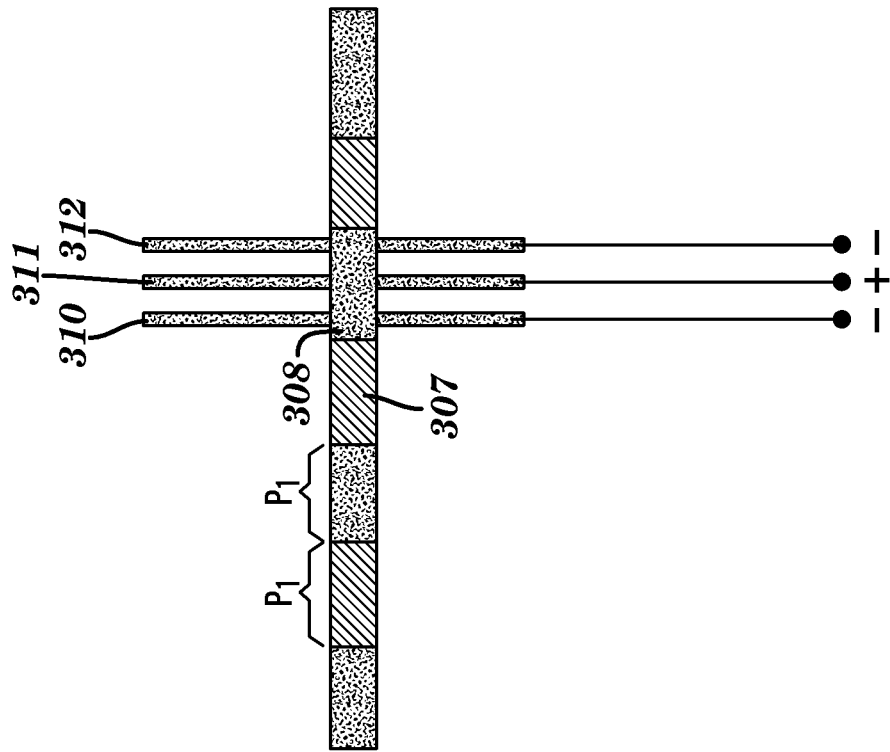
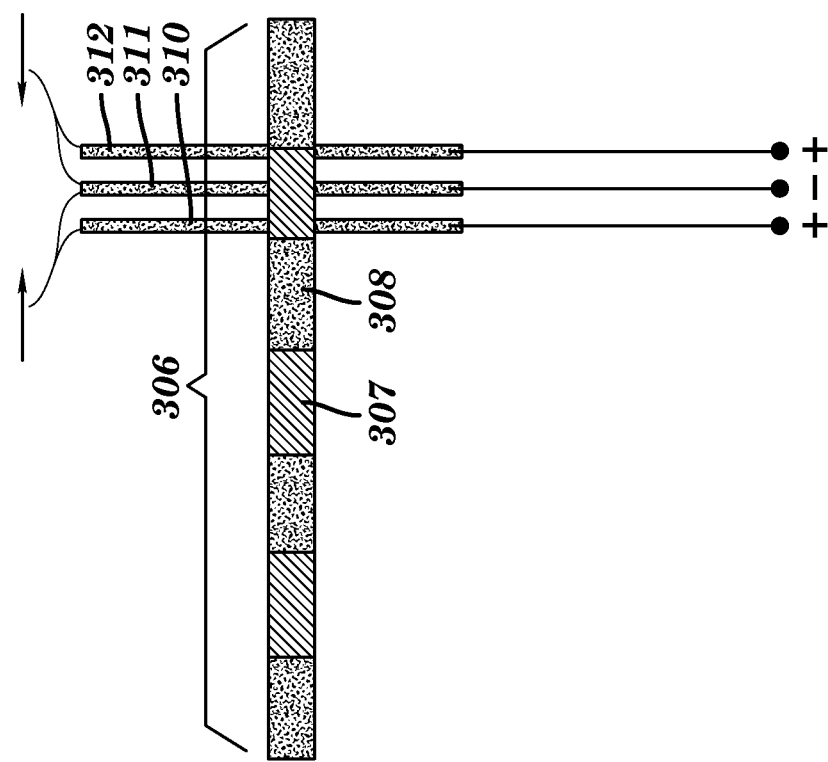

CHARGED ENTITIES AS LOCOMOTIVE TO CONTROL MOTION OF POLYMERS THROUGH A NANOCHANNEL

BACKGROUND

Exemplary embodiments relate to nanodevices, and more specifically, to controlling a polymer in a nanodevice.

Recently, there has been growing interest in applying nanopores as sensors for rapid analysis of biomolecules (e.g., polymers) such as Deoxyribonucleic acid (DNA), Ribonucleic acid (RNA), protein, etc. Emphasis has been given to applications of nanopores for DNA sequencing, as this technology holds the promise to reduce the cost of sequencing below $1000/human genome. Two issues in these applications of nanopores are the control of the translocation of DNA through the nanopore and differentiating DNA bases.

Nanopore sequencing is a technique for determining the order in which nucleotides occur on a strand of DNA. A nanopore is simply a small hole of the order of several nanometers in internal diameter. The theory behind nanopore sequencing has to do with what occurs when the nanopore is immersed in a conducting fluid and an electric potential (voltage) is applied across it: under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

DNA could be driven through the nanopore by using various approaches. For example, an electric field might attract the DNA towards the nanopore, and it might eventually pass through it. Also, enzymes attached to the nanopore might guide DNA towards the nanopore. The scale of the nanopore means that the DNA may be forced through the hole as a long string, one base at a time, like thread through the eye of a needle.

BRIEF SUMMARY

According to an exemplary embodiment, an apparatus is provided for controlling one or more charged entities through a nanochannel. The charged entities can be linked to a polymer to control the motion of the polymer through the nanochannel. The apparatus includes a first reservoir and a second reservoir connected by the nanochannel, and an array of electrodes positioned along the nanochannel. Fluid fills the first reservoir, the second reservoir, and the nanochannel. The apparatus includes a first electrode in the first reservoir and a second electrode in the second reservoir, where the first and second electrodes are configured to direct the one or more charged entities linked to the polymer into the nanochannel. The array of electrodes is configured to trap the one or more charged entities in the nanochannel responsive to being controlled for trapping, and the array of electrodes are configured to move the one or more charged entities along the nanochannel responsive to being controlled for moving.

According to an exemplary embodiment, a system is provided for controlling one or more charged entities linked to a polymer through a nanochannel. The system includes an apparatus having a first reservoir and a second reservoir connected by the nanochannel, and an array of electrodes positioned along the nanochannel. Fluid fills the first reservoir, the second reservoir, and the nanochannel. The apparatus includes a first electrode in the first reservoir and a second electrode in the second reservoir, where the first and second electrodes are configured to direct the one or more charged entities linked to the polymer into the nanochannel. Also, the system includes a voltage source configured to cause the array of electrodes to trap the one or more charged entities in the nanochannel responsive to the voltage source being controlled for trapping. The voltage source is configured to cause the array of electrodes to move the one or more charged entities along the nanochannel responsive to the voltage source being controlled for moving.

According to an exemplary embodiment, an apparatus is provided for controlling one or more charged entities through a nanochannel. The apparatus includes a first reservoir and a second reservoir connected by the nanochannel, and an array of electrodes positioned along the nanochannel. Fluid fills the first reservoir, the second reservoir, and the nanochannel. The apparatus includes a first electrode in the first reservoir and a second electrode in the second reservoir, where the first and second electrodes are configured to direct the one or more charged entities into the nanochannel. The array of electrodes is configured to trap the one or more charged entities in the nanochannel responsive to being controlled for trapping, and the array of electrodes are configured to move the one or more charged entities along the nanochannel responsive to being controlled for moving.

Additional features are realized through the techniques of the present disclosure. Other systems, methods, apparatus, and/or computer program products according to other embodiments are described in detail herein and are considered a part of the claimed invention. For a better understanding of exemplary embodiments and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features of the present disclosure are apparent from the following detailed description taken in conjunction with the accompanying drawings in which:

FIG. 4A illustrates how charged entities are trapped by three electrodes according to an exemplary embodiment.

FIG. 4B illustrates how charged entities are moved along a nanochannel with a distance corresponding to a period of the charged entities according to an exemplary embodiment.

DETAILED DESCRIPTION

Exemplary embodiments may employ an array of electrodes along a nanochannel as a "track" and charged entities/molecules (linked to a polymer) as a "locomotive" to control the motion of the polymer (such as DNA, RNA, etc.) through the nanochannel. Exemplary embodiments use an array of sensing parts to enhance the spatial resolution of reading the units of the polymer. The spatial resolution corresponds to the size of individual sensing parts, which would otherwise be limited by the relatively large size of the charged entities/molecules acting as the locomotive.

As mentioned above, exemplary embodiments are configured to link the polymer, DNA, RNA, etc., to a relatively large charged entity/molecule (or an array of relatively large charged entities/molecules) to form a molecule train, and then employ an array of electrodes along a nanochannel to control the motion of the whole train through the channel. Unlike a state of the art technique for a DNA transistor, instead of using charges naturally on the polymer, exemplary embodiments can offer more options on the locomotive part which is the engine that controls the motion of the polymer. A locomotive with higher charge density and/or larger size (than the attached polymer) would require less voltage between electrodes to trap the locomotive against thermal agitation and/or to move the locomotive along the nanochannel, thus posing less problem on the erosion of electrodes during device operation. The spatial trapping accuracy may be affected by the size of the locomotive (i.e., the charged entities/molecule(s)) as compared to the size of the individual unit of the polymer. To enhance the sensing spatial resolution to the size of a single sensing part of the array of sensing parts (i.e., an array of sensors), exemplary embodiments can monitor the signals from all the sensing parts (sensors) simultaneously and then cross-compare the signals.

Figure 1:
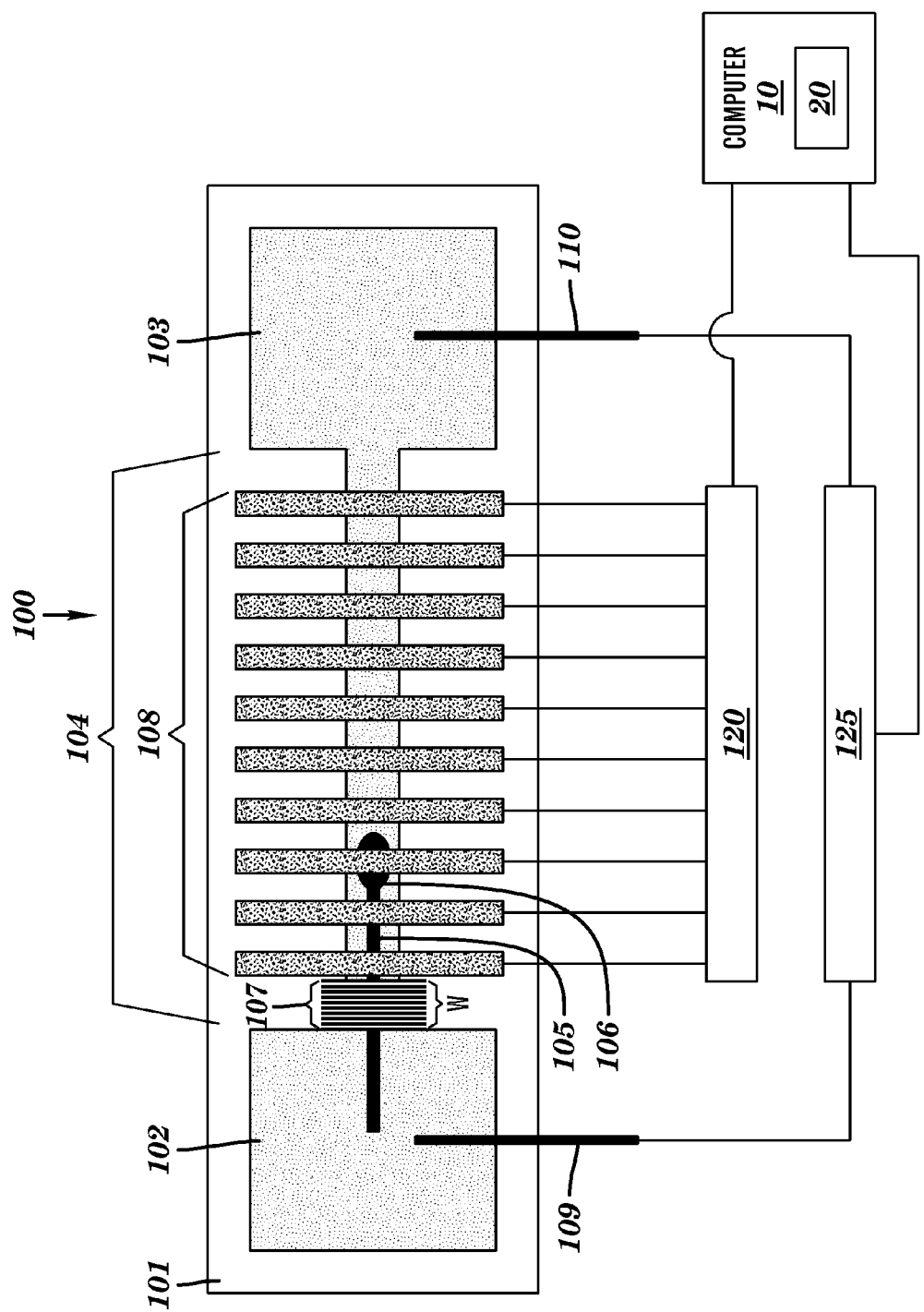
FIG. 1 depicts a cross-sectional schematic of nanochannel with an array of electrodes for controlling motion of a polymer linked to a single charged entity/molecule according to an exemplary embodiment.

Now turning to the figures, FIG. 1 illustrates a cross-sectional schematic 100 of nanochannel 104 with an array of electrodes 108 for controlling the motion of a polymer 105 linked to a single charged entity/molecule 106 (which may be referred to as a charged entity) according to an exemplary embodiment. A substrate 101 may be made of any insulating solid material including but not limited to, e.g., silicon. Two reservoirs 102 and 103 are etched into the substrate 101, with the nanochannel 104 connecting the two reservoirs 102 and 103. The reservoirs 102 and 103 and the nanochannel 104 are then filled with an ionic solution which is a conductive fluid. The polymer 105, such as DNA, RNA, etc., is made of individual units that need to be sequenced/measured. As understood by one skilled in the art, a polymer is a large molecule (macromolecule) composed of repeating structural units. These subunits are typically connected by covalent chemical bonds. The term polymer may encompass a large class comprising both natural and synthetic materials with a wide variety of properties. The polymer 105 is linked/connected to the single charged entity 106 which is the locomotive (i.e., engine) that controls the movement of the attached polymer 105. An array of sensors 107 (which is an array of sensing parts) is utilized for identifying the individual units of the polymer 105 as understood by one skilled in the art. The array of electrodes 108 is utilized for trapping the charged entity 106 (locomotive) and for controlling movement of the charged entity 106 along the nanochannel 104 in a precise manner. Each of the electrodes 108 may be made of metal. Two electrodes 109 and 110 (e.g., such as Ag or AgCl wires) are dipped in the reservoirs 102 and 103 respectively. The array of electrodes 108 are respectively connected to voltage source 120, and the two electrodes 109 and 110 are connected to voltage source 125. The voltage sources 120 and 125 are respectively controlled by software 20 in a computer 10. The voltage from the voltage source 125 is applied (via the software 20) to the electrodes 109 and 110 to move the charged entity 106 and attached polymer 105 (i.e., train) from the reservoir 102 into the nanochannel 104. The software 20 may be programmed to automatically control the timing and amount of voltage applied by the voltage source 120 and the voltage source 125, and the software 20 may also include a user interface configured for a user to control the same.

Figure 2B:
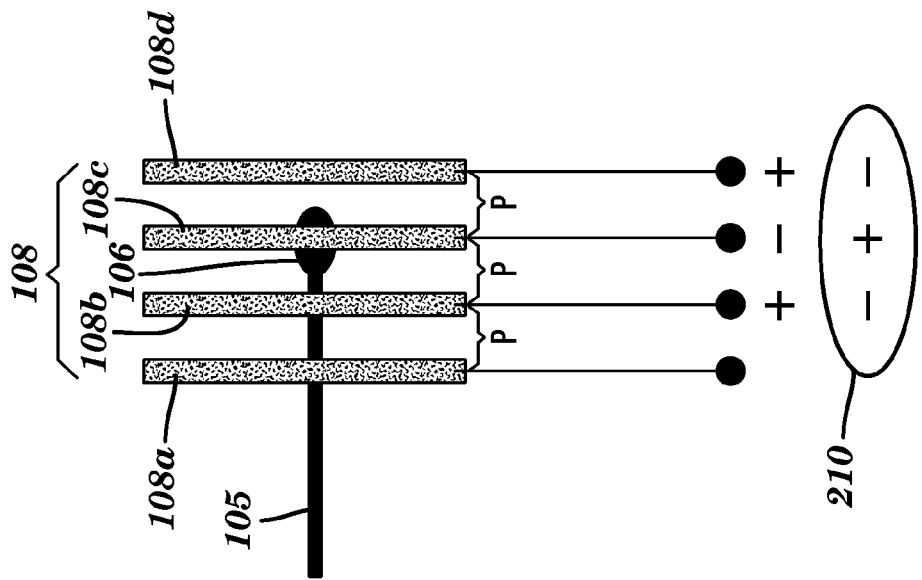
FIG. 2B illustrates how a charged entity is moved along a nanochannel with a distance corresponding to a period of an array of electrodes according to an exemplary embodiment.
Figure 2A:
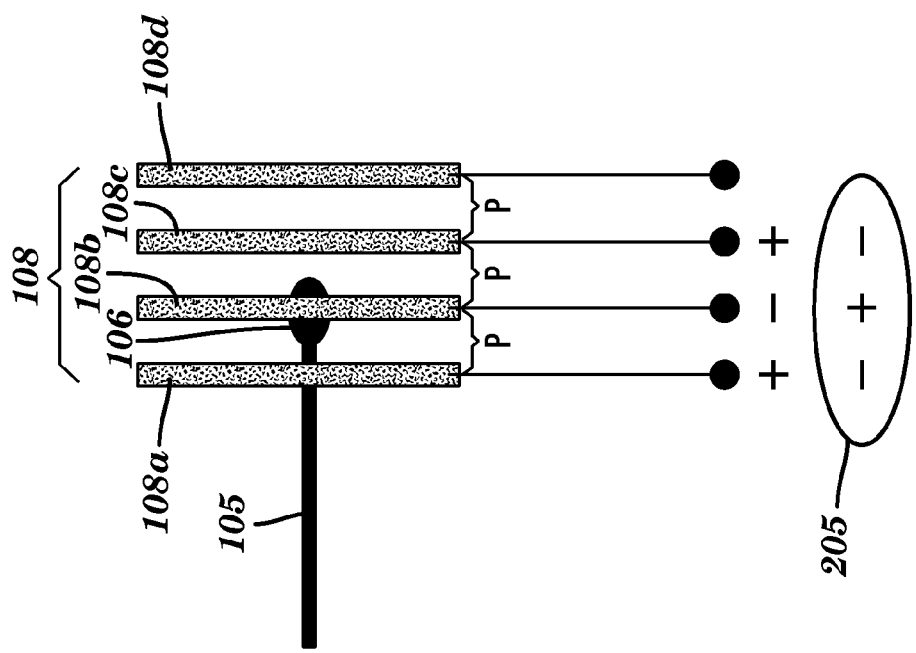
FIG. 2A illustrates how a charged entity is trapped by three metal electrodes according to an exemplary embodiment.

FIG. 2A illustrates how the charged entity 106 (i.e., locomotive) is trapped by three electrodes 108 according to an exemplary embodiment. For explanation purposes, the three electrodes 108 are designated as electrodes 108a, 108b, and 108c. At this point, during trapping, no voltage is applied to the remaining electrodes 108 in the array including a fourth electrode designated as electrode 108d for explanation purposes as shown in FIG. 2A. Although only four electrodes 108a, 108b, 108c, and 108d are illustrated in FIGS. 2A and 2B, it is contemplated that numerous electrodes 108 may be utilized as track to control the movement and trapping of the charged entity 106 attached to the polymer 105 through the nanochannel 104. For example, there should be enough electrodes in the array of electrodes 108 to ensure that the entire polymer 105 being tested passes through the array of sensors 107. Also, during trapping no voltage bias is applied to electrodes 109 and 110.

Assuming the charged entity 106 is positively charged, the software 20 is configured to apply a polarity scheme of a positive voltage bias (via the voltage source 120) on the first electrode 108a (counting from left to right) and the third electrode 108c, relative to the second electrode 108b having a negative voltage bias applied thereto. As such, the positively charged entity 106 (locomotive) will be pinned down (i.e., trapped) by the electrical fields between electrodes 108a, 108b, and 108c. The positively charged entity 106 is attracted to the electrode 108b (having a negative voltage bias applied thereto) against thermal motion/agitation. For example, if the positively charged entity 106 were caused (by thermal motion and/or any other force) to move to the left, the electrode 108a would repel the positively charged entity 106 back to the electrode 108b. Likewise, if the positively charged entity 106 were caused (by thermal motion and/or any other force) to move to the right, the electrode 108c would repel the positively charged entity 106 back to the electrode 108b. By this effect, the polymer 105 (attached to the back end of the charged entity 106 like a train car) is trapped in position by the electrodes 108a, 108b, and 108c, such that the units of the polymer 105 are read/measured by the array of sensors 107. The array of sensors 107 may be controlled and operated by the software 20 in the computer 10. In one implementation, the software 20 is configured to control the array of sensors 107 to apply a voltage from voltage source 130 (shown in FIG. 1) to the units of the polymer 105 that are within a width W (area) of the array of sensors 107. Then, the software 20 is configured to read individual current output through each of the units of the polymer 105 (via current meter 135) within the width W of the array of sensors 107.

FIG. 2B illustrates how the charged entity 106 (i.e., acting as the locomotive) is moved along the nanochannel 104 with a distance of a period P of the array of electrodes 108 according to an exemplary embodiment. The period P is the distance measured between (the center of) one electrode 108 to (the center of) the preceding and/or succeeding electrode 108. For example, the distance between each electrode 108 is equal such that the period P between each electrode 108 has the same distance measurement. The distance of the width W of the array of sensors 107 is greater than or equal to the distance of the period P between each electrode 108; accordingly, each time the polymer 105 moves a distance corresponding to a period P, there is some overlap of the units of the polymer 105 that have already been measured with the new units of the polymer 105 to be measured (i.e., the units of the polymer 105 that have not yet made it to the width W of the array of sensors 107).

By applying (via the software 20 of the computer 10 in FIG. 1) the same polarity scheme of the voltage biases on the next set (e.g., shifted to the right by one electrode) of three metal electrodes 108b, 108c, and 108d, the charged entity 106 will move to the center of the three electrodes 108b, 108c, and 108d. That is, the charged entity 106 will be attracted to electrode 108c. Also, during the moving stage, the voltage bias is applied to electrodes 109 and 110 to break the previous trap (symmetry) in FIG. 2A and to cause the charged entity 106 to move (or begin moving) in the right direction. In this case, the software 20 is configured to apply a positive voltage bias to electrode 108b (where previously a negative voltage bias was applied to electrode 108b in FIG. 2A) and electrode 108d (where previously no voltage bias was applied to electrode 108d and any subsequent electrodes), and is configured to apply a negative voltage bias to electrode 108c (where previously a positive voltage bias was applied to electrode 108c in FIG. 2A). By shifting the polarity scheme of the voltage bias (up by a single electrode 108 in the array of electrode 108) from electrodes 108a, 108b, 108c to electrodes 108b, 108c, 108d, the charged entity 106 moved by one period P. Since from electrode 108b to electrode 108c is one period of the array of electrodes 108, the (locomotive) positively charged entity 106 will move along the nanochannel 104 with a distance of the period P of the array of electrodes 108. As the (locomotive) positively charged entity 106 and the polymer 105 are thermally agitated, the trapping shown in FIG. 2A and the movement shown in FIG. 2B will have an accuracy, which can be maintained/guaranteed to be better than the period P of the array of the electrodes 108 if suitable voltage biases are applied between the (metal layers) electrodes 108 (in the manner illustrated in FIGS. 2A and 2B). The suitable voltage biases applied to the array of electrodes 108 for trapping and moving the charged entity 106 are greater that the thermal energy kT which is 26 milli-electron volts (meV), where k is Boltzmann's constant and T is absolute temperature.

Utilizing the array of sensors 107, the software 20 is configured to detect each of the signals output from all the sensing parts (of the array of sensors 107) simultaneously and then cross-compare the output signals (e.g., electrical currents). In this way, the software 20 is configured to determine a spatial resolution defined by the period $P_{sensor}$ of the individual sensors of the array of sensors 107. The period $P_{sensor}$ of the array of sensors 107 is the distance between each sensor (each sensor 107 is illustrated with a dark vertical line in the width W). The period $P_{sensor}$ of the array of sensors 107 is designed to be equal or less than the spacing/distance between the units of the polymer 105. For example, if one implements the array of sensors 107 by using a carbon nanotube array (with a 2 nm (nanometer) diameter for individual carbon nanotubes and a 2 nm gap between the carbon nanotubes) as sensing electrodes (i.e., individual sensors), this array of sensors 107 would have a spatial resolution of 4 nm.

Although examples herein may describe trapping and moving a positively charged entity in FIGS. 2A and 2B (as well as FIGS. 4A and 4B), exemplary embodiments are not limited to using a positively charged entity(s). In a case where the charged entity 106 is negatively charged, the voltage biases (i.e., polarity scheme) shown in FIGS. 2A and 2B would be those shown in circles 205 and 210. In such a case, the negatively charged entity 106 would be attracted to a positive voltage bias applied to electrode 108b and trapped in place between (and repelled from) the negative voltage bias applied to the electrodes 108a and 108c. To move (i.e., shift to the right by one period P) the negatively charged entity 106, the voltage biases applies to electrodes 108b, 108c, and 108d should have the polarity shown in circle 210 of FIG. 2B. At this point, the negatively charged entity 106 would have moved (one period P) from being previously pinned/trapped by electrode 108a to being trapped by electrode 108b.

This process of trapping and moving the charged entity 106 via the software 20 may continue until the charged entity 106 has pulled the attached polymer 105 completely through the array of sensors 107 for measuring/sequencing the units of the polymer 105. As such, the process of shifting the voltage bias polarity scheme to the next consecutive ones of the electrodes 108 continues. During the process of shifting the voltage bias polarity scheme down the array of electrodes 108, one subsequent electrode 108 (such as the electrode 108a) no longer receives a voltage bias while a next electrode 108 (such as the electrode 108d) receives a voltage bias in the array of electrodes 108, until the charged entity 106 has moved down all of the electrodes 108 (similar to how a locomotive moves down the train track).

In certain embodiments, the charged entity 106 can be either charged biomolecules or charged solid state particles. Charged biomolecules can range in size and weight from a single spherical protein such as albumen (BSA) all the way to large complex proteins. An example of a charged metal containing protein (e.g., 12 nm in diameter) is ferritin. This protein has an exterior protein shell called apoferritin and an inner core that is made of iron hydroxide in varying amounts. Having a core with varying amounts of metal hydroxide will allow one to manipulate the molecule because of the charge variability. Other charged solid state particles, such as Au (gold) or Ag (silver) particles can be wrapped with a protein shell such as streptavidin, which can be linked to the polymer 105 such as DNA via streptavidin-biotin bond.

Figure 3:
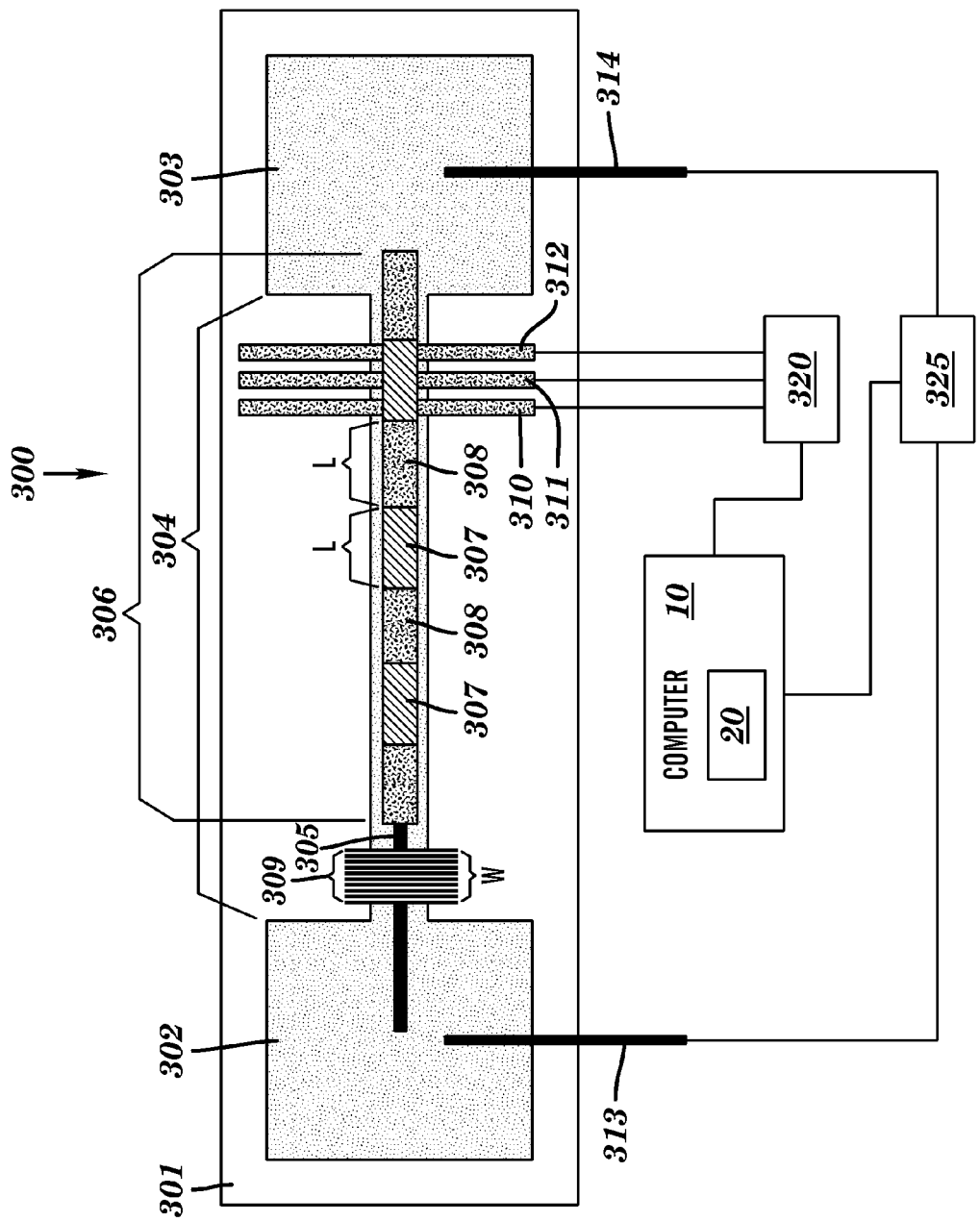
FIG. 3 depicts a cross-sectional schematic of a nanochannel with three electrodes for controlling motion of a polymer linked to an array of charged entities/molecules according to an exemplary embodiment.

FIG. 3 illustrates a cross-sectional schematic 300 of a nanochannel 304 with three electrodes 310, 311, and 312 (e.g., an array of electrodes) for controlling the motion of a polymer 305 linked to an array of charged entities/molecules 306 according to an exemplary embodiment. Unlike FIG. 1, which utilizes more than three electrodes 108 to continue moving the charged entity along the array of electrodes 108, FIG. 3 utilizes (only) the three electrodes 310, 311, and 312 to move the charged entity without requiring additional electrodes as a further track. The electrodes 310, 311, and 312 may be made of metal.

A substrate 301 may be made of any insulating solid material. Two reservoirs 302 and 303 are etched into the substrate 301, with the nanochannel 304 connecting the reservoirs 302 and 303. The reservoirs 302 and 303 and the nanochannel 304 are then filled with ionic solution, such as a conductive fluid. As discussed above, the polymer 305, such as DNA, RNA, etc., is made of individual units that need to be sequenced/measured.

The polymer 305 is linked to an array of charged entities/molecules 306 which acts as the locomotive to pull the attached polymer 305 through the nanochannel 304. The charged entities 306 include an array of one or more charged parts 307 and one or more uncharged (i.e., neutral) parts 308. In one implementation, the charged entities 306 may include an array of charged parts (as charged parts 307) and neutral parts (as uncharged parts 308). In other implementation, the charged entities 306 may include an array of positively charged parts (as charged parts 307) and negatively charged parts (as uncharged parts 308), or vice versa. The charged parts 307 and uncharged parts 308 repeat in an alternating fashion to form the array of charged entities 306 as shown in FIG. 3. An array of sensors 309 (like the array of sensors 107) is utilized for identifying the individual units of the polymer 305. As controlled by the software 20 of the computer 10, the three electrodes 310, 311 and 312 are utilized for trapping the (locomotive) charged entities 306 and for controlling the movement of the charged entities 306 (pulling and stopping the polymer 305) along the nanochannel 304 in a precise manner.

Two electrodes 313 and 314, such as Ag or AgCl wires, are dipped in the two reservoirs 302 and 303 respectively. The electrodes 310, 311, and 312 are respectively connected to voltage source 320, and the two electrodes 313 and 314 are connected to voltage source 325. The voltage sources 320 and 325 are respectively controlled by software 20 in the computer 10. The voltage from the voltage source 325 is applied (via the software 20) to the electrodes 313 and 314 to move the train of the charged entities 306 and polymer 305 (from the reservoir 302) into the nanochannel 304.

FIG. 4A illustrates how the charged entities 306 acting as the locomotive are trapped by three metal electrodes 310, 311, and 312 according to an exemplary embodiment. Assuming the charged part 307 (of the charged entities 306) is positively charged, the software 20 is configured to apply a positive voltage bias to the electrodes 310 and 312 via the voltage source 320, relative to the electrode 311 having a negative voltage bias applied thereto. As shown in FIG. 4A, the first polarity scheme of the voltage bias applied to electrodes 310, 311, and 312 is positive-negative-positive respectively. The positively charged part 307 of the charged entities 306 will move to the center area of the three electrodes 310, 311, and 312 and be pinned down there by the electrical fields, as shown in FIG. 4A (while applying voltage to electrodes 313 and 314 during the moving and no voltage to electrodes 313 and 314 during the trapping).

By this effect, the polymer 305 (attached to the back end of the charged entities 306 like a train car) is trapped in position by the electrodes 310, 311, and 312, such that the units of the polymer 305 are measured/sequenced by the array of sensors 309. The array of sensors 309 may be controlled and operated by the software 20 in the computer 10. In one implementation, the software 20 is configured to control the array of sensors 309 to apply a voltage from a voltage source (not shown) to the units of the polymer 305 that are within an area of the width W of the array of sensors 309. Then, the software 20 is configured to read individual current (i.e., signals) output through each of the units of the polymer 305 (via a current meter not shown) within the width W of the array of sensors 309.

At this point, the positively charged part 307 is trapped by the voltage biases applied to the three electrodes 310, 311, and 312 according to the first polarity scheme, and no voltage bias is applied to electrodes 313 and 314. If thermal motion/agitation attempts to cause the positively charged part 307 to move to the left, an electric field pointing to the right and exerting a force in the right direction (resulting from electrodes 310 and 311) causes the positively charged part 307 (or uncharged part 308 when it is trapped) to move back to the right. That is, the electric field pointing in the right direction counteracts the thermal motion to the left. Likewise, if thermal motion/agitation attempts to cause the positively charged part 307 (or uncharged part 308 when it is trapped) to move to the right, an electric field pointing to the left and exerting a force in the left direction (resulting from electrodes 311 and 312) causes the positively charged part 307 to move back to the left. That is, the electric field pointing in the left direction counteracts the thermal motion to the right. As result of the electric fields exerted by electrodes 310, 311, 312, respectively having the positive, negative, positive voltage bias of the voltage source 320 applied by the software 20, the three electrodes 310, 311, and 312 trap the positively charged part 307 (an inverted polarity scheme is utilized to trap the uncharged part 308). As a result, the attached polymer 305 is trapped for measurement by the array of sensors 309. When the voltage bias is applied to electrodes 310, 311, and 312 via the voltage source 320 to trap the positively charged part 307 (or the uncharged part 308 (i.e., neutral) as discussed further below), the voltage bias applied via voltage source 325 to electrodes 313 and 314 is turned off.

FIG. 4B illustrates how the charged entities 306 (acting as the locomotive) are moved along the nanochannel 304 with a distance corresponding to the period $P_1$ of the charged entities 306 (i.e., array of charged entities/molecules) in accordance with an exemplary embodiment. For simplicity, each charged part 307 is drawn in equal length to each uncharged part 308 (as one implementation), but the charged part 307 and uncharged part 308 do not have to be the same length. The period $P_1$ is the average of the length of each of the repeating/alternating charged parts 307 and the length of each of the repeating/alternating uncharged parts 308 that form the charged entities 306.

By inverting the first polarity scheme (as shown in FIG. 4A) to the second polarity scheme shown in FIG. 4B for the voltage biases applied to the three metal electrodes 310, 311, and 312, the uncharged part 208 of the charged entities 306 will move to the center area of three electrodes 310, 311, and 312; also, the voltage bias on electrodes 313 and 314 is initially applied to break the trap (symmetry) in FIG. 4A, but will be turned off when the uncharged part 208 is in (or near) the trapping area of the three electrodes 310, 311, 312. In this way, the charged entities 306 (acting as the locomotive for the attached polymer 305) moves along the nanochannel 304 with a distance of the period $P_1$ of the charged entities 306 each time the polarity scheme alternates. For example, the charge entities 306 are fed (to the right) through the area of the three electrodes 310, 311, and 312 as the polarity scheme alternates from the first polarity scheme, then to the second polarity scheme, back to the first polarity scheme, and so forth. The alternating of the polarity scheme by the software 20 causes the charged part 307 and uncharged part 308 to each move one period $P_1$.

As the charged entities 306 and the attached polymer 305 are thermally agitated, the trapping shown in FIG. 4A and the movement shown in FIG. 4B will have an accuracy that can be maintained to be better than the period $P_1$ of the array of electrodes 310, 311, and 312 if suitable voltage biases applied between the electrodes (metal layers) 310, 311, and 312. As discussed above, the voltage biases applied to the electrodes 310, 311, and 312 for trapping and moving the charged entities 306 are greater that the thermal energy kT which is 26 milli-electron volts (meV), where k is Boltzmann's constant and T is absolute temperature. The thermal energy causes the thermal motion/agitation.

Utilizing the array of sensors 309, the software 20 is configured to detect the signals output from all the individual sensors 309 simultaneously and then cross-compare the output signals received at each of the sensors 309. In this way, the software 20 can determine a spatial resolution defined by the period $P_{sensor}$ of the sensors 309. The period $P_{sensor}$ of the array of sensors 309 is the distance between each sensor (e.g., each sensor is shown with a dark vertical line in the width W). The period $P_{sensor}$ of the array of sensors 309 is designed to be equal or less than the spacing/distance between the units of the polymer 305. The units of the polymer 305 are not shown but one skilled in the art understands that the spacing/distance between the units of the polymer 305 is based on the type of polymer being tested. For example, if one implements the array of sensors 309 by using a carbon nanotube array (with 2 nm diameter for individual carbon nanotubes and a 2 nm gap between the carbon nanotubes) as sensing electrodes (i.e., individual sensors 309), this array of sensors 309 would have a spatial resolution of 4 nm.

Referring to FIG. 4B, when the first polarity scheme of the voltage biases is switched to (the second polarity scheme) the negative voltage bias for electrode 310, the positive voltage bias for electrode 311, and the negative voltage bias for the electrode 312, the positively charged part 307 is moved to the right and the uncharged part 308 is moved into the area of the three electrodes 310, 311, and 312; as such, the uncharged part 308 is trapped in the area of the three electrodes 310, 311, and 312, thus trapping the attached polymer 305 at its location for measurement by the array of sensors 309. When the second polarity scheme is switched back, the next positively charged part 307 is moved into the area of the electrodes 310, 311, and 312. Also, as noted herein, if the uncharged part 308 is charged, but with a different polarity (charge) than the charged part 307, the above motion control application will still as discussed above. Accordingly, the charged part 307 and the uncharged part 308 are not meant to be limited.

As an exemplary embodiment, the charged part 307 may be DNA oligonucleotide while the uncharged part 308 may be polyethylene glycol. One skilled in the art can readily select a desired charged and uncharged part in accordance with the teaching of the present disclosure.

As mentioned previously, DNA sequencing is one application of the present disclosure. Current lithography technology, such as nanoimprint lithography, can yield sub-10 nm features for electrodes, which will guarantee sub-10 nm accuracy for trapping. This may be applicable for DNA sequencing technologies based on modification of a DNA sample (e.g., the polymer) that requires positional control of sub-10 nm accuracy.

Figure 5:
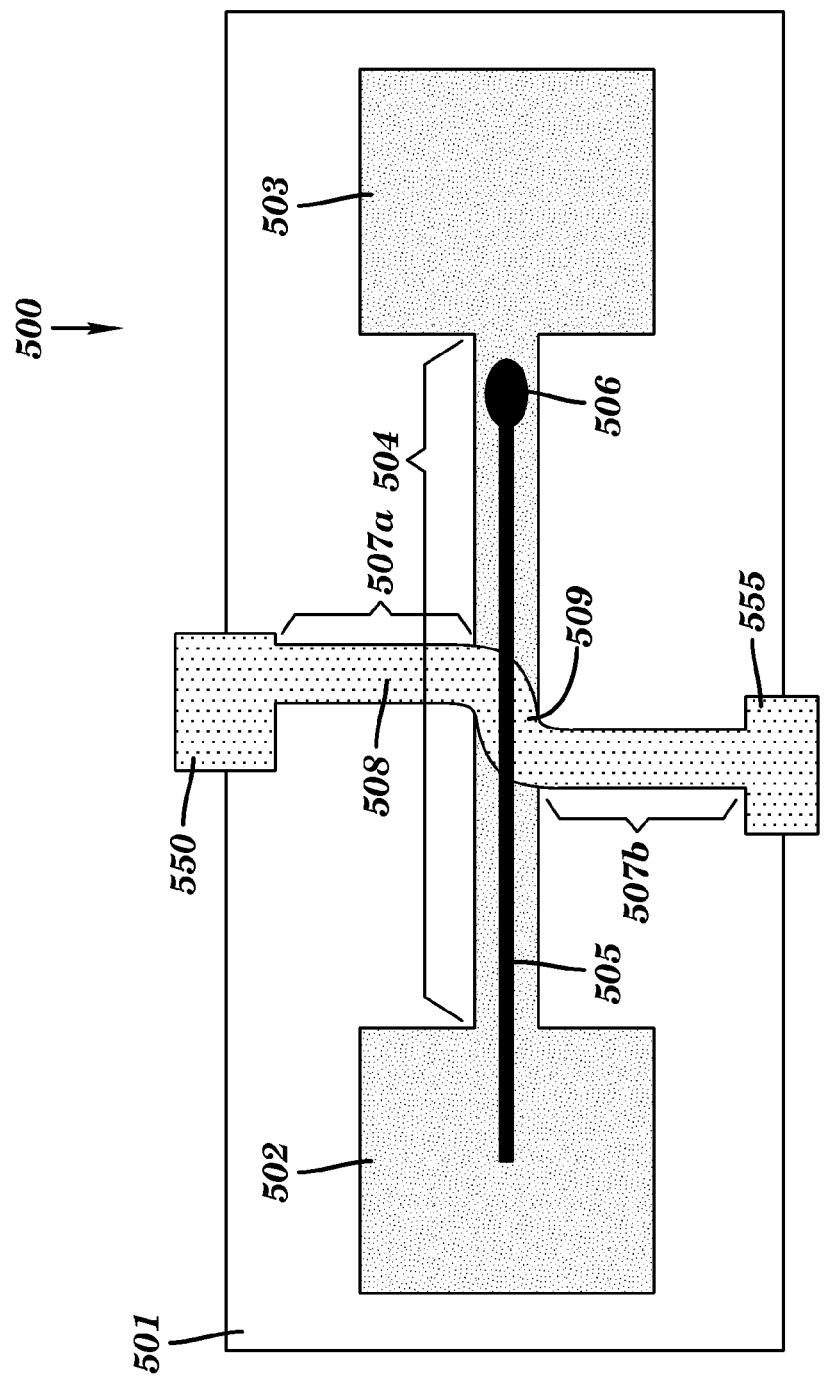
FIG. 5 depicts a cross-sectional schematic of a nanochannel for localized chemical treatment/synthesis of a polymer while the position of the polymer is controlled in the nanochannel according to an exemplary embodiment.

As exemplary embodiments are configured to control the motion of a charged entity, which in turn controls the polymer linked to it, the polymer can be any polymer (including charged and uncharged polymers). This builds the foundation for another exemplary application, which is localized chemical treatment and/or synthesis to the polymer while the position of the polymer is controlled, as illustrated in FIG. 5. According to an exemplary embodiment, FIG. 5 illustrates a cross-sectional schematic 500 that includes elements described with reference to FIG. 1 or 3 but not repeated for conciseness. Elements 501, 502, 503, 504, 506 are the same as elements 101, 102, 103, 104, 105, 106 in FIG. 1 or elements 301, 302, 303, 304, 305, 306 in FIG. 3. Accordingly, their operation is as discussed herein. For simplicity and not limitation, the additional elements in FIG. 1 or 3 for controlling the motion of the charged entity 506 attached to the polymer 505 are not shown in FIG. 5 but are contemplated to be part of and functionally integrated in the exemplary embodiment described in FIG. 5.

Newly added fluid nanochannels 507a and 507b are two additional nanochannels (as compared to FIGS. 1 and 3). The nanochannel 504 contains ionic fluid as discussed above for nanochannels 104 and 304. Nanochannels 507a and 507b are physically connected to nanochannel 504 to communicatively exchange fluids. Reagents 508 (that are chemically designed to react with polymer 505 as desired) are loaded into the nanochannel 504 through nanochannel 507a and then flushed out though nanochannel 507b. If the flow rate in nanochannel 507b is higher than that of nanochannel 507a, reagents 508 will be confined in the local area 509 in nanochannel 504. The size of local area 509 can be tuned by the ratio of the flow rate in nanochannel 507b to the flow rate in nanochannel 507a. For example, the flow rate in nanochannel 507a can be increased to thus cause a larger area 509; likewise, the flow rate in nanochannel 507a can be reduced to cause a smaller area 509. After reaction by the reagents 508 which may be a predetermined time based on chemical properties of the reagents 508, the reagents 508 will be quickly flushed out with the same ionic buffer in reservoirs 502 and 503; this guarantees local modification of the polymer 505 just at the local area 509. Using the trapping and movement techniques described in FIGS. 1, 2A, 2B, 3, 4A, and 4B, the exact location on the polymer 505 to apply the reagents 508 can be precisely defined/selected by trapping and then moving the polymer 505 through the nanochannel 504 accordingly. By controlling the movement (stopping and going) of the polymer 505 at precise locations as desired, other locations on the polymer 505 can also be selectively, locally modified by repeatedly loading reagents 508 from the nanochannel 507a and flushing the reagents 508 out the into the nanochannel 507b while the polymer 505 is controllably moved to a new location in the nanochannel 504.

In one implementation, to control loading and removing the reagents 508 in and out of the local area 509, an injector 550 may be communicatively attached to the end of the nanochannel 507a while a collector 555 is communicatively attached to the end of the nanochannel 507b. The injector 550 may be a pump that applies positive pressure to the reagents 508 in the nanochannel 507a which causes the reagents 508 to flow through the area 509 onto the part of the polymer 505 in that area for the desired reaction. The collector 555 may be a pump that applies a negative pressure to the reagents 508 in the nanochannel 507b which causes the reagents 508 that flowed through the area 509 to be withdrawn (i.e., the reagents 508 in the nanochannel 504 are suctioned out of the nanochannel 504 by the negative pressure and flowed into the nanochannel 507b). The nanochannels 507a and 507b may be physically connected to nanochannel 504 via an aperture at the local area 509. In another implementation, the injector 550 and the collector 555 may be integrated as a single unit. The operation of the injector 550 and collector 555 may be controlled by the software 20 in the computer 10 (shown in FIGS. 1 and 3).

As an example for explanation purposes, the polymer 505 may be a DNA strand, while reagents 508 may be hydroxyl radical which can break the DNA backbone. Using the above approach in FIG. 5, the DNA can be cut at any of the specified locations. In accordance with the present disclosure, it is understood by one skilled in the art that different reagents 508 may be utilized to affect a desired polymer 505 at specific locations as controllably selected. Accordingly, the selection of the polymer and reagents are not meant to be limited.

Figure 6:
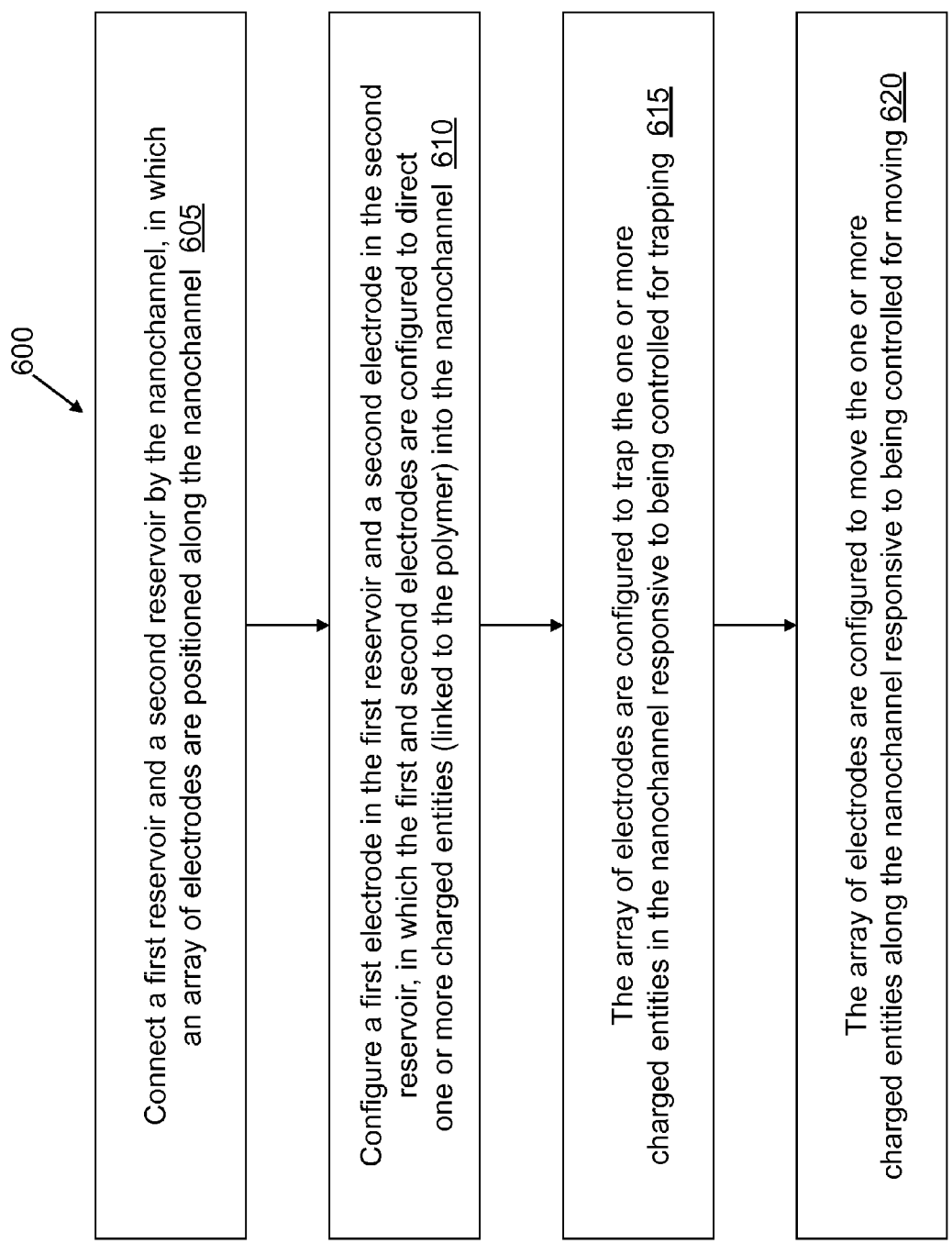
FIG. 6 is a method for controlling one or more charged entities linked to a polymer through a nanochannel according to an exemplary embodiment.

FIG. 6 illustrates a method 600 for controlling one or more charged entities linked to a polymer through a nanochannel according to an exemplary embodiment. Reference can be made to FIGS. 1, 2A, 2B, 3, 4A, 4B, and 5. The software 20 is configured to control the trapping and moving of the one or more charged entities.

At block 605, a first reservoir (e.g., reservoir 102, 302, 502) and a second reservoir (e.g., reservoir 103, 303, 503) are connected by the nanochannel (e.g., nanochannel 104, 304, 504), and an array of electrodes (e.g., array of electrodes 108, 310, 311, 312) are positioned along the nanochannel in which fluid (e.g., ionic fluid) fills the first reservoir, the second reservoir, and the nanochannel.

A first electrode (e.g., electrode 109, 313) is in the first reservoir and a second electrode (e.g., electrode 110, 314) is in the second reservoir, in which the first and second electrodes are configured to direct the one or more charged entities (e.g., charged entities 106, 306, 506) linked to the polymer (e.g., polymer 105, 305, 505) into the nanochannel at block 610.

The array of electrodes are configured to trap the one or more charged entities in the nanochannel (as shown in FIGS. 2A, 2B, 4A, 4B) when controlled for trapping at block 615. Also, the array of electrodes are configured to move the one or more charged entities along the nanochannel (as shown in the shift from FIGS. 2A to 2B and FIGS. 4A to 4B) when controlled for movement at block 620.

Further, the array of electrodes (e.g., electrodes 108, 310, 311, 312) are configured to trap the one or more charged entities in the nanochannel in response to a voltage bias being applied to the array of electrodes as controlled by the software 20 as shown in FIGS. 2A, 2B, 4A, 4B.

With reference to FIGS. 4A and 4B, the array of electrodes are configured to move the one or more charged entities 306 along the nanochannel one period (e.g., period P or period $P_1$) at a time in response to a voltage bias being applied to the array of electrodes. The one or more charged entities 306 comprise a charged part 307 and an uncharged part 308, in which the charged part 307 and the uncharged part 308 have an equal length L. One period $P_1$ corresponds to the equal length L of the charged part 307 and the uncharged part 308. Alternating a polarity scheme (such as positive-negative-positive to negative-positive-negative (and vice versa) by the software 20) of the voltage bias applied to the individual electrodes of the array of electrodes causes the one or more charged entities 306 to move along the nanochannel for one period $P_1$ at a time (by trapping and moving as shown in FIGS. 4A and 4B). The array of electrodes are configured to trap the charged part 207 in an area of the array of electrodes or to move the uncharged part 208 from the area (e.g., when shifting from negative-positive-negative to positive-negative-positive, the uncharged part 208 is shifted out of the area and the charged part 207 is then trapped in the area) of the array of electrodes in response to the voltage bias being applied with a first polarity scheme (e.g., positive-negative-positive). Likewise, the array of electrodes are configured to trap the uncharged part 208 in the area of the array of electrodes or to move the charged part 207 from the area (e.g., when shifting from positive-negative-positive to negative-positive-negative, the charged part 207 is shifted out of the area and the uncharged part 208 is then trapped in the area) of the array of electrodes in response to the voltage bias being applied with a second polarity scheme (negative-positive-negative).

With reference to FIGS. 2A and 2B, the one period P corresponds to an equal distance between individual electrodes in the array of electrodes 108. The voltage bias having a polarity scheme (e.g., positive-negative-positive) is applied to a consecutive group (e.g., electrodes 108a, 108b, 108c) of the individual electrodes of the array of electrodes to move the one or more charged entities 106 along the nanochannel for the equal distance of the one period P. Also, the voltage bias having the polarity scheme (e.g., positive-negative-positive) is applied to another consecutive group (e.g., electrodes 108b, 108c, 108d) of the individual electrodes of the array of electrodes 108 to move the one or more charged entities 106 along the nanochannel for the equal distance of the one period P. The other consecutive group (e.g., electrodes 108b, 108c, and 108d) is shifted up one individual electrode as compared to the consecutive group of electrodes. In other words, the polarity scheme continues to shift up the track of electrodes 108 to concurrently move the one or more charged entities 106 in the same direction as the shifting.

With reference to FIG. 5, additional nanochannels (e.g., nanochannels 507a and 507b) are filed with another fluid (e.g., a reagent) to react with the polymer 505, and the nanochannels 507a and 507b are in communication with the nanochannel 504 through an area 509. The nanochannel 507a is configured to expel the other fluid (i.e., reagent) into the nanochannel 504 to react with the polymer 505 at the localized area 509, in response to a positive pressure applied (e.g., by injector 550) to the nanochannel 507a. Conversely, nanochannel 507b is configured to draw in the other fluid out that has been expelled into the nanochannel 504 at the localized area 509, in response to negative pressure applied (e.g., by collector 555) to the nanochannel 507b.

Figure 7:
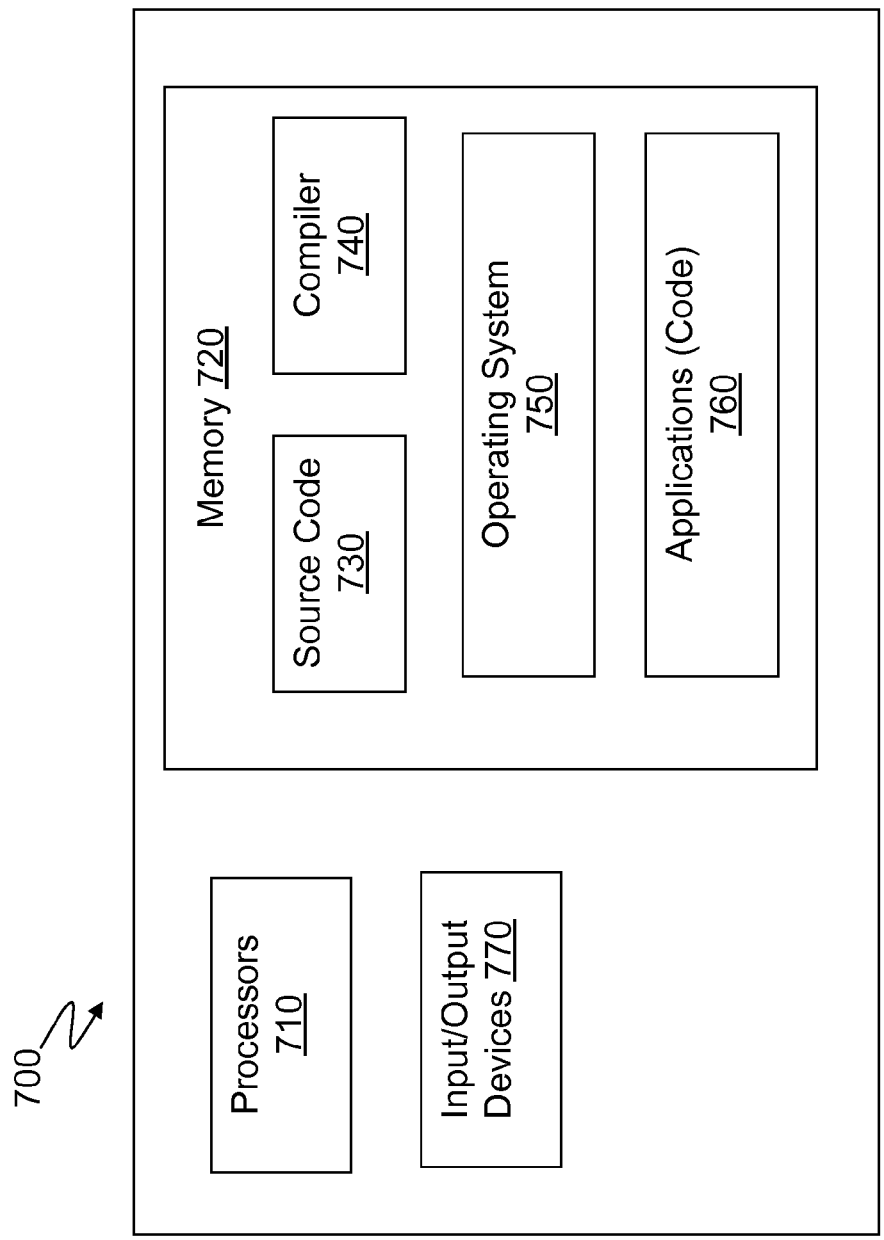
FIG. 7 depicts a computing system having features that may be utilized according to an exemplary embodiment.

FIG. 7 illustrates an example of a computer system 700 having capabilities, which may be included in exemplary embodiments. Various methods, procedures, modules, flow diagrams, tools, application, and techniques discussed herein may also incorporate and/or utilize the capabilities of the computer system 700. Moreover, capabilities of the computer system 700 may be utilized to implement features of exemplary embodiments discussed herein with reference to FIGS. 1-6. One or more of the capabilities of the computer system 700 may implement any element discussed herein such as but not limited to the software 20 and the computer 10.

Generally, in terms of hardware architecture, the computer system 700 may include one or more processors 710, computer readable storage memory 720, and one or more input and/or output (I/O) devices 770 that are communicatively connected via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 710 is a hardware device for executing software that can be stored in the memory 720. The processor 710 can be virtually any custom made or commercially available processor, a central processing unit (CPU), a data signal processor (DSP), or an auxiliary processor among several processors associated with the computer system 700.

The computer readable memory 720 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 720 may incorporate electronic, magnetic, optical, and/or other types of storage media. Note that the memory 720 can have a distributed architecture, where various components are situated remote from one another, but can be accessed by the processor 710.

The software in the computer readable memory 720 may include one or more separate programs, each of which comprises an ordered listing of executable instructions for implementing logical functions. The software in the memory 720 includes a suitable operating system (O/S) 750, compiler 740, source code 730, and one or more applications 760 of the exemplary embodiments. As illustrated, the application 760 comprises numerous functional components for implementing the features, processes, methods, functions, and operations of the exemplary embodiments. Further, the application 760 may be a source program, executable program (object code), script, or any other entity comprising a set of instructions to be performed.

The I/O devices 770 may include input devices (or peripherals) such as, for example but not limited to, a mouse, keyboard, scanner, microphone, camera, etc. Furthermore, the I/O devices 770 may also include output devices (or peripherals), for example but not limited to, a printer, display, etc. Finally, the I/O devices 770 may further include devices that communicate both inputs and outputs, for instance but not limited to, a NIC or modulator/demodulator (for accessing remote devices, other files, devices, systems, or a network), a radio frequency (RF) or other transceiver (tower), a telephonic interface, a bridge, a router, etc. The I/O devices 770 also include components for communicating over various networks, such as the Internet or an intranet. The I/O devices 770 may be connected to and/or communicate with the processor 710 utilizing Bluetooth connections and cables (via, e.g., Universal Serial Bus (USB) ports, serial ports, parallel ports, fiber optics, FireWire, HDMI (High-Definition Multimedia Interface), etc.).

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. An apparatus for controlling one or more charged entities linked to a polymer through a nanochannel, the apparatus comprising:
    a first reservoir and a second reservoir connected by the nanochannel, an array of electrodes being positioned along the nanochannel, wherein fluid fills the first reservoir, the second reservoir, and the nanochannel; and
    a first electrode in the first reservoir and a second electrode in the second reservoir, the first and second electrodes being configured to direct the one or more charged entities linked to the polymer into the nanochannel;
    wherein the array of electrodes is configured to trap the one or more charged entities in the nanochannel responsive to being controlled for trapping;
    wherein the array of electrodes is configured to move the one or more charged entities along the nanochannel responsive to being controlled for moving;
    wherein the array of electrodes is configured to move the one or more charged entities along the nanochannel one period at a time in response to shifting a voltage bias being applied to the array of electrodes;
    wherein the voltage bias having a polarity scheme is applied to a triplet electrode group, all at one time, in the array of electrodes to trap a single charged entity attached to the one or more charged entities in the nanochannel in which the triplet electrode group is simultaneously aligned to and corresponds to the single charged entity; and
    wherein the polarity scheme to trap the single charged entity includes positive and negative voltage biases applied to the triplet electrode group according to a charge of the single charged entity;
    wherein the triplet electrode group has a first electrode, a second electrode, and a third electrode;
    wherein, when the single charged entity is positively charged, the polarity scheme applied to the triplet electrode group is a positive voltage bias, a negative voltage bias, and a positive voltage bias respectively for the first electrode, the second electrode, and the third electrode; and
    wherein, when the single charged entity is negatively charged, the polarity scheme applied to the triplet electrode group is a negative voltage bias, a positive voltage bias, and a negative voltage bias respectively for the first electrode, the second electrode, and the third electrode.

2. The apparatus of claim 1, wherein the array of electrodes is configured to trap the one or more charged entities in the nanochannel in response to a voltage bias being applied to the array of electrodes.

3. The apparatus of claim 1, wherein the one or more charged entities comprise an array of at least a charged part and an uncharged part, and
    wherein the one period corresponds to an average of a length of the charged part and a length of the uncharged part.

4. The apparatus of claim 3, wherein alternating a polarity scheme of the voltage bias applied to individual electrodes of the array of electrodes causes the one or more charged entities to move along the nanochannel for the one period at a time.

5. The apparatus of claim 3, wherein the array of electrodes is configured to trap the charged part in a center area of the array of electrodes or to move the uncharged part from the center area of the array of electrodes in response to the voltage bias being applied with a first polarity scheme; and
    wherein the array of electrodes is configured to trap the uncharged part in the center area of the array of electrodes or to move the charged part from the center area of the array of electrodes in response to the voltage bias being applied with a second polarity scheme.

6. The apparatus of claim 1, wherein the one period corresponds to an equal distance between individual electrodes in the array of electrodes.

7. The apparatus of claim 6, wherein the voltage bias having the polarity scheme is applied to another triplet electrode group of the individual electrodes in the array of electrodes to move the one or more charged entities along the nanochannel for the equal distance of the one period; and wherein the another triplet electrode group is shifted up by one of the individual electrodes as compared to the consecutive group.

8. The apparatus of claim 1, further comprising another nanochannel filed with another fluid to react with the polymer, the another nanochannel being in communication with the nanochannel by an opening;

wherein the opening is configured to expel the another fluid into the nanochannel to react with the polymer at a localized area around the opening, in response to a positive pressure applied to the another nano channel; and wherein the opening is configured to draw in the another fluid that has been expelled into the nanochannel at the localized area around the opening, in response to negative pressure applied to the another nanochannel.

9. The apparatus of claim 1, wherein the one or more charged entities comprise an array of charged parts and neutral parts.

10. The apparatus of claim 1, wherein the one or more charged entities comprise an array of positively charged parts and negatively charged parts.

11. A system for controlling one or more charged entities linked to a polymer through a nanochannel, the system comprising:

an apparatus comprising:

a first reservoir and a second reservoir connected by the nanochannel, an array of electrodes being positioned along the nanochannel, wherein fluid fills the first reservoir, the second reservoir, and the nanochannel;

a first electrode in the first reservoir and a second electrode in the second reservoir, the first and second electrodes being configured to direct the one or more charged entities linked to the polymer into the nanochannel; and a voltage source configured to cause the array of electrodes to trap the one or more charged entities in the nanochannel responsive to the voltage source being controlled for trapping;

wherein a voltage bias having a polarity scheme is applied via the voltage source to a triplet electrode group, all at one time, in the array of electrodes to trap a single charged entity attached to the one or more charged entities along the nanochannel in which the triplet electrode group is simultaneously aligned to and corresponds to the single charged entity;

wherein the polarity scheme to trap the single charged entity includes positive and negative voltage biases applied to the triplet electrode group according to a charge of the single charged entity;

wherein the voltage source is configured to cause the array of electrodes to move the one or more charged entities along the nanochannel responsive to the voltage source being controlled for moving;

wherein the triplet electrode group has a first electrode, a second electrode, and a third electrode;

wherein, when the single charged entity is positively charged, the polarity scheme applied to the triplet electrode group is a positive voltage bias, a negative voltage bias, and a positive voltage bias respectively for the first electrode, the second electrode, and the third electrode; and wherein, when the single charged entity is negatively charged, the polarity scheme applied to the triplet electrode group is a negative voltage bias, a positive voltage bias, and a negative voltage bias respectively for the first electrode, the second electrode, and the third electrode.

12. The system of claim 11, wherein the array of electrodes is configured to trap the one or more charged entities in the nanochannel in response to the voltage bias being applied to the array of electrodes.

13. The system of claim 11, wherein the array of electrodes is configured to move the one or more charged entities along the nanochannel one period at a time in response to the voltage bias being applied to the array of electrodes.

14. The system of claim 13, wherein the one or more charged entities comprise a charged part and an uncharged part; and wherein the one period corresponds to an average of a length of the charged part and a length of the uncharged part.

15. An apparatus for controlling one or more charged entities through a nanochannel, the apparatus comprising:

a first reservoir and a second reservoir connected by the nanochannel, an array of electrodes being positioned along the nanochannel, wherein fluid fills the first reservoir, the second reservoir, and the nanochannel; and a first electrode in the first reservoir and a second electrode in the second reservoir, the first and second electrodes being configured to direct the one or more charged entities into the nanochannel;

wherein the array of electrodes is configured to trap the one or more charged entities in the nanochannel responsive to being controlled for trapping;

wherein a voltage bias having a polarity scheme is applied to a triplet electrode group, all at one time, in the array of electrodes to trap a single charged entity attached to the one or more charged entities along the nanochannel in which the triplet electrode group is simultaneously aligned to and corresponds to the single charged entity;

wherein the polarity scheme to trap the single charged entity includes positive and negative voltage biases applied to the triplet electrode group according to a charge of the single charged entity;

wherein the array of electrodes is configured to move the one or more charged entities along the nanochannel responsive to being controlled for moving;

wherein the triplet electrode group has a first electrode, a second electrode, and a third electrode;

wherein, when the single charged entity is positively charged, the polarity scheme applied to the triplet electrode group is a positive voltage bias, a negative voltage bias, and a positive voltage bias respectively for the first electrode, the second electrode, and the third electrode; and wherein, when the single charged entity is negatively charged, the polarity scheme applied to the triplet electrode group is a negative voltage bias, a positive voltage bias, and a negative voltage bias respectively for the first electrode, the second electrode, and the third electrode.

\* \* \* \* \*